US012655419B2

(12) United States Patent
Davis et al.

(10) Patent No.: US 12,655,419 B2
(45) Date of Patent: Jun. 16, 2026

(54) METHODS FOR CHARACTERIZATION OF VIRAL GENOME USING BASE MODIFICATIONS

(71) Applicant: Regeneron Pharmaceuticals, Inc., Tarrytown, NY (US)

(72) Inventors: Steven Davis, East Greenbush, NY (US); Jared Richardson, Valley Falls, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 630 days.

(21) Appl. No.: 18/122,246

(22) Filed: Mar. 16, 2023

(65) Prior Publication Data

US 2023/0295608 A1    Sep. 21, 2023

Related U.S. Application Data

(60) Provisional application No. 63/320,951, filed on Mar. 17, 2022.

(51) Int. Cl.
*C12Q 1/6869* (2018.01)
*C12N 15/10* (2006.01)

(52) U.S. Cl.
CPC ....... *C12N 15/1065* (2013.01); *C12Q 1/6869* (2013.01)

(58) Field of Classification Search
None
See application file for complete search history.

(56) References Cited

FOREIGN PATENT DOCUMENTS

WO      13/148400 A1    10/2013

OTHER PUBLICATIONS

Radukic et al. Nanopore sequencing of native adeno-associated virus (AAV) single-stranded DNA using a transposase-based rapid protocol. NAR Genomics and Bioinformatics 2(4): 1 (2020). (Year: 2020).*
Mochizuki et al. A simple and sensitive method for determining the strand orientation of single-stranded viral genomes. Journal of Virological Methods 185:149-151 (2012). (Year: 2012).*
Toth et al., "Methylation Status of the Adeno-Associated Virus Type 2 (AAV2)", Viruses, vol. 11, No. 1, Jan. 9, 2019 (Jan. 9, 2019) p. 38, XP093058222, DOI: 10.3390/v11010038.
WIPO Application No. PCT/US2023/015345, PCT International Search Report and Written Opinion of the International Searching Authority mailed Jul. 13, 2023.

* cited by examiner

*Primary Examiner* — Samuel C Woolwine
(74) *Attorney, Agent, or Firm* — Schwabe, Williamson & Wyatt PC; David Mellman

(57)            ABSTRACT

Methods for assaying a sample of viral particles comprising a single-stranded DNA genome for strand-specificity are disclosed. In embodiments, the methods include synthesis of a synthetic DNA strand complementary to the single-stranded DNA genome by incorporating a modified base to yield a labeled double-stranded DNA product, purification of the labeled double-stranded DNA product, sequencing of the purified double-stranded DNA product on a sequencer, and determining the specificity of the viral single-stranded DNA genome based on the detection of the modified base of the synthetic DNA strand.

26 Claims, 6 Drawing Sheets

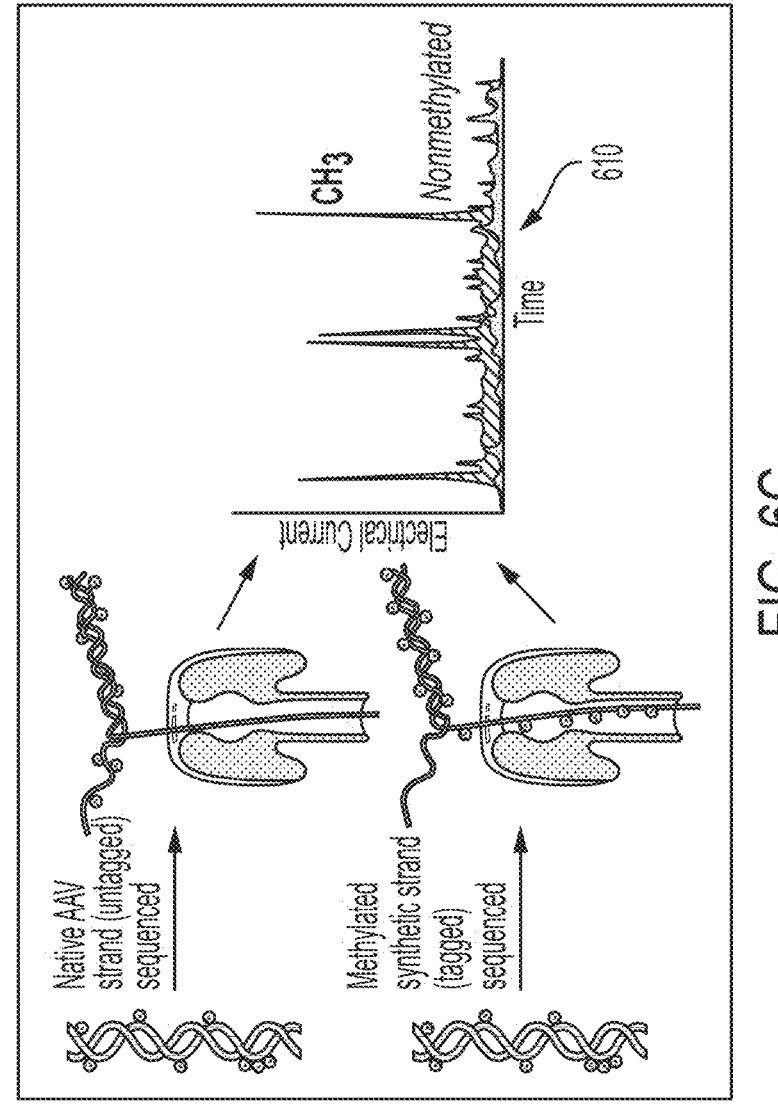
FIG. 6C
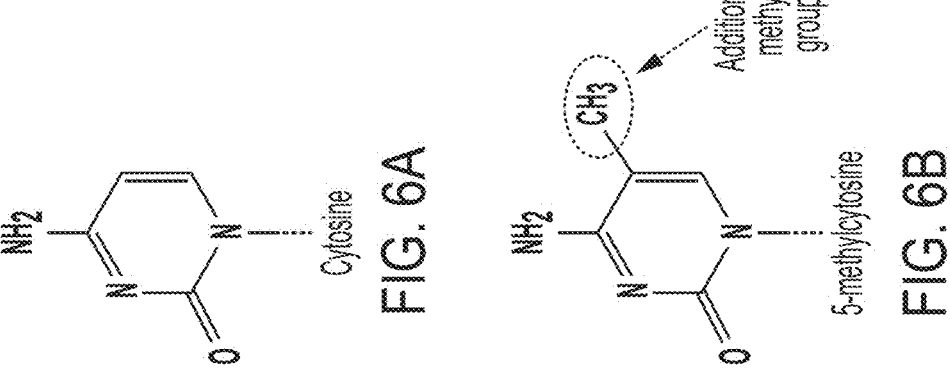
FIG. 6A
FIG. 6B

METHODS FOR CHARACTERIZATION OF VIRAL GENOME USING BASE MODIFICATIONS

CROSS-REFERENCE TO RELATED APPLICATION

This application claims the benefit under 35 USC § 119(e) of U.S. Provisional Application No. 63/320,951, filed Mar. 17, 2022, which is incorporated herein by reference in its entirety for all purposes.

FIELD OF THE INVENTION

The present invention relates to methods for characterization of viral genome and packaging (e.g., AAV genome) using modified bases.

BACKGROUND

Adeno-associated virus (AAV), which is a non-enveloped, single-stranded DNA virus, has emerged as an attractive class of therapeutic agents to deliver genetic materials to host cells for gene therapy, due to its ability to transduce a wide range of species and tissue in vivo, low risk of immunotoxicity, and mild innate and adaptive immune responses. Recombinant AAV technology relies on proper genome packaging, which can be in both sense and anti-sense conformations. A standard method for assessing the DNA content packaged into AAV particles is not yet known. Existing methods allow characterization of structural anomalies in AAV packaging in self-complimentary AAV variants; however, they do not provide an in-depth analysis of single-stranded AAV genome that accounts for its strand-specificity. The complex nature of viral vectors such as AAV require advanced methods to enable product testing and characterization. Thus, methods are needed to determine the specificity of the single-stranded DNA of the viral particles.

BRIEF SUMMARY OF THE INVENTION

The present disclosure is directed to a method for single-stranded DNA strand differentiation that preserves strand-specific information in a sample of viral particles (e.g., AAV) using a combination of modified base incorporation and long-read sequencing approach. In exemplary embodiments, a modified base such as 5-methylcytosine (5mC) is used to label single-stranded DNA which is detected by a nanopore sequencer platform, allowing the identification of the specificity of the sequenced strand. The selective labeling of single DNA strands of viral genome and their subsequent analysis uniquely enables viral gene therapy quality control at the molecular level in a quantitative fashion, and adds an additional resolution to analysis of single-stranded viral constructs.

In one aspect, the present disclosure provides a method for assaying a sample of viral particles comprising a single-stranded DNA genome for strand-specificity, comprising: (a) synthesizing a synthetic DNA strand complementary to a native DNA strand of the sample of viral particles to yield a double-stranded DNA product, the synthetic DNA strand being synthesized by incorporating a modified base; (b) purifying the synthesized double-stranded DNA product; (c) sequencing the purified double-stranded DNA product on a sequencer, wherein the sequencer identifies the sequence of nucleotides in one sequenced strand of the double-stranded DNA product; and (d) determining the specificity of the native DNA strand by identifying the specificity of the sequenced strand, and detecting whether the sequenced strand contains the modified base, wherein the presence of the modified base indicates that the sequenced strand is the synthetic DNA strand of the double-stranded DNA product.

In some embodiments, the sample of viral particles comprises adeno-associated virus (AAV) particles. In some cases, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

In some embodiments, the modified base comprises 5-methylcytosine, 5-hydroxymethylcytosine, or N6-methyl-deoxyadenosine. In some cases, the modified base is 5-methylcytosine.

In some embodiments, incorporation of the modified base causes the synthetic DNA strand to be methylated.

In some embodiments, the double-stranded DNA product is purified using magnetic beads.

In some embodiments, the sequencer is a nanopore sequencer.

In some embodiments, the nanopore sequencer allows entry of either the native DNA strand or the selectively labeled synthetic DNA strand of the purified double-stranded DNA product for sequencing.

In some embodiments, the native DNA strand or the selectively labeled synthetic DNA strand is sequenced using a long-read sequencing approach.

In some embodiments, the modified base of the synthetic DNA strand is detected by an alteration of a flow of current through the nanopore sequencer. In some cases, detection of the modified base distinguishes the synthetic DNA strand from the native DNA strand entering the nanopore sequencer.

In some embodiments, the method further comprises identifying a percentage of sense strand and anti-sense strand packaged in the sample of viral particles based on detection of the modified base of the synthetic DNA strand.

In one aspect, the present disclosure provides a method for distinguishing between a native DNA strand and a synthetic DNA strand in a sample of adeno-associated virus (AAV) particles comprising a single-stranded DNA genome, comprising: (a) synthesizing the synthetic DNA strand complementary to the native DNA strand to yield a double-stranded DNA product, the synthetic DNA strand including a modified base which selectively labels the synthetic DNA strand; (b) purifying the double-stranded DNA product; (c) sequencing the purified double-stranded DNA product on a nanopore sequencer; and (d) determining the specificity of the native DNA strand by identifying the specificity of the sequenced strand, and detecting whether the sequenced strand contains the modified base of the synthetic DNA strand during nanopore sequencing by detecting an alteration of a flow of current through the nanopore sequencer, wherein the presence of the modified base indicates that the sequenced strand is the synthetic DNA strand of the double stranded DNA product.

In some embodiments, the modified base comprises 5-methylcytosine, 5-hydroxymethylcytosine, or N6-methyl-deoxyadenosine. In some cases, the modified base is 5-methylcytosine.

In some embodiments, the selective labeling causes the synthetic DNA strand to be methylated.

In some embodiments, the native DNA strand or the selectively labeled synthetic DNA strand is sequenced using a long-read sequencing approach.

In some embodiments, the double-stranded DNA product is purified using magnetic beads.

In some embodiments, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

In some embodiments, the method further comprises determining an orientation of the sequenced strand based on detection of the modified base of the synthetic DNA strand.

In some embodiments, the method further comprises identifying a proportion of each of a sense strand and an anti-sense strand packaged in the sample of adeno-associated virus (AAV) particles based on determination of the orientation of the sequenced strand.

In some embodiments, the viral particles comprise an exogenous gene in the single-stranded DNA genome. In some cases, the exogenous gene is a therapeutic gene.

In some embodiments, the method further comprises determining a complete sequence of the sequenced strand.

In some embodiments, the method further comprises identifying a complementary nucleotide sequence corresponding to the complete sequence, if the sequenced strand is the synthetic DNA strand of the double stranded DNA product.

In any of the various embodiments discussed above or herein, sequencing of the nucleic acid identifies from about 100 to about 5000 nucleotides in the sequenced strand. In some cases, the sequencing identifies from 100 to 1000 nucleotides in the sequenced strand. In some cases, the sequencing identifies from 100 to 500 nucleotides in the sequenced strand.

In any of the various embodiments discussed above or herein, sequencing of the nucleic acid is performed without fragmentation of the sequenced strand.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

BRIEF DESCRIPTION OF THE DRAWINGS

FIGS. 6A and 6B illustrate the chemical structures of unmodified base cytosine and modified base 5-methylcytosine, respectively.

FIG. 6C illustrates sequencing of selectively labeled versus unlabeled DNA strands via a nanopore sequencer, wherein detection of an altered flow of current indicates the presence of the modified base 5-methylcytosine. "Me" or "CH$_3$" refers to methylated.

DETAILED DESCRIPTION

Figure 1:
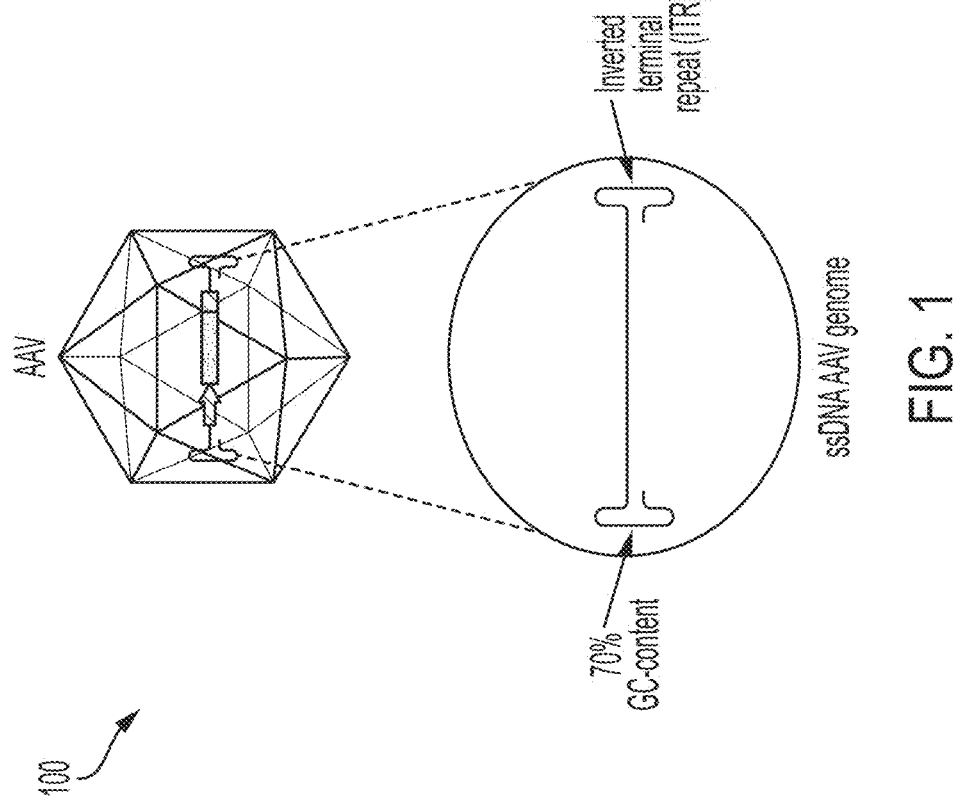
FIG. 1 illustrates an AAV capsid with a single-stranded DNA genome comprising a therapeutic gene or gene of interest (GOI).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "include," "includes," and "including," are meant to be non-limiting and are understood to mean "comprise," "comprises," and "comprising," respectively.

Although any methods and materials similar or equivalent to those described herein can be used in the practice or testing of the present invention, the preferred methods and materials are now described. All patents, applications and non-patent publications mentioned in this specification are incorporated herein by reference in their entireties.

Selected Abbreviations

AAV: Adeno-Associated Virus
ssDNA: single-stranded DNA
dsDNA: double-stranded DNA
GOI: gene of interest
PCR: polymerase chain reaction
5mC: 5-methylcytosine
dNTPs: Deoxyribonucleotide triphosphate
dATP: Deoxyadenosine triphosphate
dGTP: Deoxyguanosine triphosphate
dTTP: Deoxythymidine triphosphate
dCTP: Deoxycytidine triphosphate
NFW: Nuclease-free water

Definitions

"Adeno-associated virus" or "AAV" is a non-pathogenic parvovirus, with single-stranded DNA, a genome of approximately 4.7 kb, not enveloped and has icosahedric conformation. AAV was first discovered in 1965 as a contaminant of adenovirus preparations. AAV belongs to the Dependovirus genus and Parvoviridae family, requiring helper functions from either herpes virus or adenovirus for replication. In the absence of helper virus, AAV can set up latency by integrating into human chromosome 19 at the 19q13.4 location. The AAV genome consists of two open reading frames (ORF), one for each of two AAV genes, Rep and Cap. The AAV DNA ends have a 145-bp inverted terminal repeat (ITR), and the 125 terminal bases are palindromic, leading to a characteristic T-shaped hairpin structure.

The term "sample," as used herein, refers to a mixture of viral particles (e.g., AAV particles) that comprises at least one viral capsid component encapsulating single-stranded DNA genome that is subjected to manipulation in accordance with the methods of the invention, including, for example, selective labeling and sequencing.

The term "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups.

A "recombinant viral particle" refers to a viral particle including one or more exogenous gene or heterologous sequences (e.g., a nucleic acid sequence not of viral origin) that may be flanked by at least one viral nucleotide sequence.

A "recombinant AAV particle" refers to a adeno-associated viral particle including one or more heterologous sequences (e.g., a nucleic acid sequence not of AAV origin) that may be flanked by at least one, for example, two, AAV inverted terminal repeat sequences (ITRs). Such rAAV particles can be replicated and packaged when present in a host cell that has been infected with a suitable helper virus (or that is expressing suitable helper functions) and that is expressing AAV rep and cap gene products (i.e., AAV Rep and Cap proteins).

A "viral particle" refers to a viral particle composed of at least one viral capsid protein and an encapsulated viral genome.

"Heterologous" or "exogenous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral particle is a heterologous or exogenous nucleotide sequence with respect to the viral particle.

The term "therapeutic gene" refers to a genetically modified gene that produces a therapeutic effect (e.g., by encoding a protein of interest), or the treatment of disease by repairing or reconstructing defective genetic material.

An "inverted terminal repeat" or "ITR" sequence is a relatively short sequence found at the termini of viral genomes which are in opposite orientation. An "AAV inverted terminal repeat (ITR)" sequence is an approximately 145-nucleotide sequence that is present at both termini of a single-stranded AAV genome.

The term "isolated," as used herein, refers to a biological component (such as a nucleic acid, peptide, protein, lipid, viral particle or metabolite) that has been substantially separated, produced apart from, or purified away from other biological components in the cell of the organism in which the component naturally occurs or is transgenically expressed.

A "vector," as used herein, refers to a recombinant plasmid or virus that comprises a nucleic acid to be delivered into a host cell, either in vitro or in vivo.

The term "corresponding" is a relative term indicating similarity in position, purpose or structure.

The term "read" with regard to sequencing refers to the nucleic acid sequence of a cluster of nucleotides that is obtained after the end of the sequencing process and which is ultimately the sequence of a section of a complete nucleic acid sequence. A "read" is the base called value of a string of nucleotides derived from a raw signal.

The term "long-read sequencing" refers to a DNA sequencing technique which can determine a sequence of nucleotides of long sequences of DNA of from about 100 base pairs to about 1,000,000 base pairs or more at a time (the upper limit may depend only on the genome being sequenced), thereby eliminating the need to fragment and amplify DNA normally required in other DNA sequencing techniques. In one example, the AAV genome (which is on the order of 5000 base pairs) can be sequenced in its entirety without any fragmentation.

As used herein, "amplification" refers to the production of multiple copies of a segment of DNA or RNA. Amplification is usually induced by polymerase chain reaction.

As used herein, "PCR" refers to polymerase chain reaction which is a molecular biology technique used to amplify a single copy of a segment of DNA or RNA, generating thousands to millions of copies of a particular DNA or RNA sequence. PCR is commonly used to amplify the number of copies of a DNA or RNA segment for cloning or to be used in other analytical procedures.

The term "nanopore sequencing" refers to sequencing of a nucleic acid molecule due to alteration of flow of current by each base as the nucleic acid molecule passes through a nanopore.

The term "strand-specificity" refers to positive or sense strand and negative or anti-sense strand of a viral genome. The positive or sense strand is the coding strand, while the negative or anti-sense strand is the non-coding strand of a gene.

General Description

The present disclosure provides methods for synthetic DNA strand synthesis and labeling by incorporation of a modified base, and sequencing the labeled synthetic DNA strand provides rapid identification of strand-specificity of ssDNA genome of a sample of viral particles (e.g., AAV particles). The present methods utilize a long-read sequencing based approach on a nanopore sequencer to identify and quantitate strand-specificity of a viral genome. Quantitative characterization to identify a proportion of each of a sense strand and an anti-sense strand packaged in the sample of AAV particles is necessary to ensure product quality and consistency, thereby greatly streamlining the quality control process.

Methods for Identifying and Quantifying Strand-Specificity of Viral Single-Stranded DNA Genome Aspects of the disclosure are directed to methods for identifying and quantifying strand-specificity of a ssDNA genome in a sample of viral particles (e.g., recombinant AAV particles) using a combination of modified base incorporation and long-read sequencing approach.

In some cases, the method comprises: (a) synthesizing a synthetic DNA strand complementary to a native DNA strand of the sample of viral particles to yield a double-stranded DNA product, the synthetic DNA strand being synthesized by incorporating a modified base; (b) purifying the synthesized double-stranded DNA product; (c) sequencing the purified double-stranded DNA product on a sequencer, wherein the sequencer identifies the sequence of nucleotides in one sequenced strand of the double-stranded DNA product; and (d) determining the specificity of the native DNA strand by identifying the specificity of the sequenced strand, and detecting whether the sequenced strand contains the modified base, wherein the presence of the modified base indicates that the sequenced strand is the synthetic DNA strand of the double-stranded DNA product.

An adeno-associated viral particle 100 along with its single-stranded DNA genome is illustrated in FIG. 1. In the example shown in FIG. 1, the ssDNA genome of AAV is highly symmetrical with palindromic elements. In addition, the ssDNA genome of AAV comprises approximately 70% GC-content with inverted terminal repeats. In some examples, the single-stranded DNA genome of a recombinant AAV may comprise a therapeutic gene or gene of interest (GOI) for the purposes of gene therapy, for example.

Figure 2:
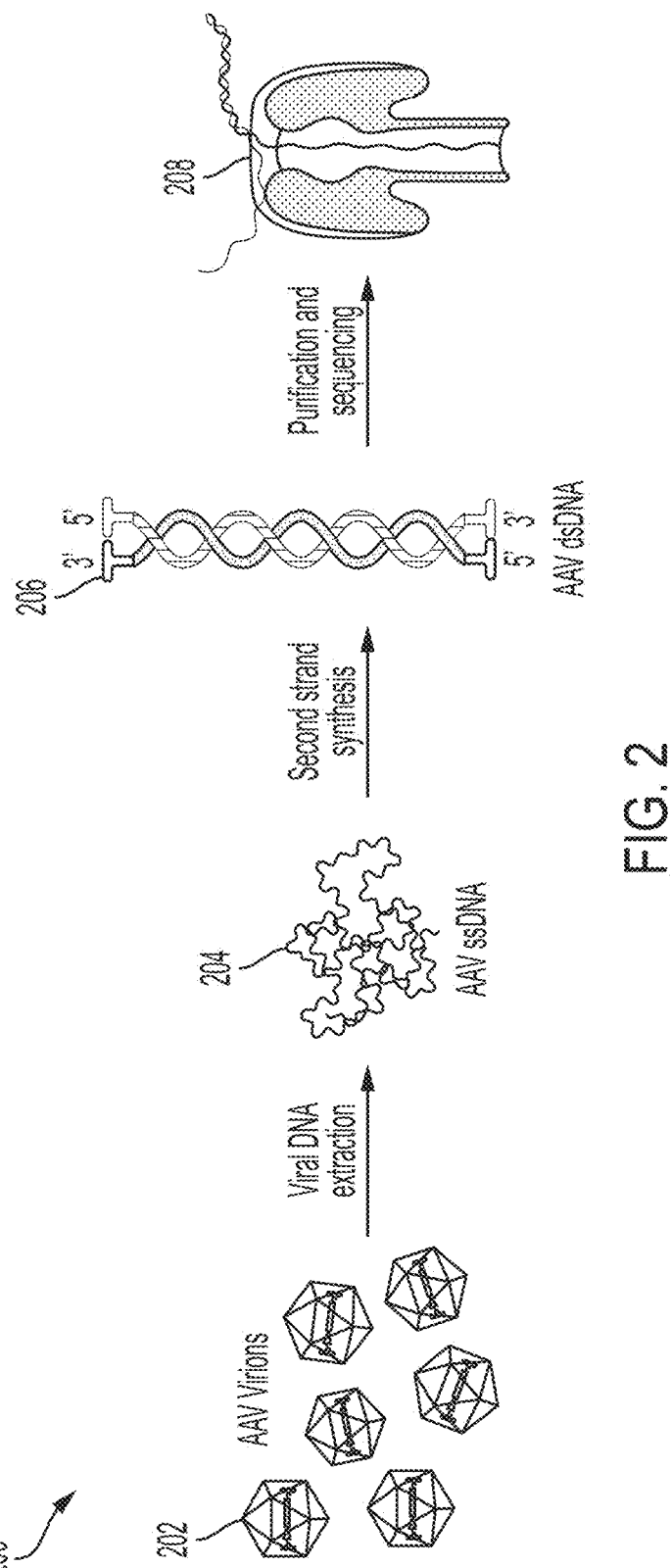
FIG. 2 illustrates an overview of an exemplary method for assaying AAV particles for strand-specificity in accordance with an embodiment of the present disclosure.

In the methods disclosed herein, method 200 for assaying AAV particles for strand-specificity is exemplified by the schematic illustrated in FIG. 2. In the example method shown in FIG. 2, ssDNA genome 204 is extracted or isolated from a sample of AAV particles 202. In one example, the isolated ssDNA genome 204 may be prepared by lysing nucleocapsids and releasing viral ssDNA using phenol-chloroform extraction, while in other examples the isolated ssDNA genome 204 may be prepared by alkaline lysis extraction. The isolated ssDNA genome 204 is then subjected to synthetic DNA strand synthesis or second strand synthesis with incorporation of a modified base to yield a selectively labeled double-stranded DNA 206. The labeled double-stranded DNA 206 is purified from the second strand synthesis reaction. In one example, the purification of the double-stranded DNA 206 may be performed using magnetic beads. Subsequently, the purified double-stranded DNA 206 is sequenced on a nanopore sequencer 208, wherein the sequencer identifies the sequence of nucleotides in one sequenced strand of the double-stranded DNA product. More details regarding second strand synthesis, purification of labeled double-stranded DNA, and nanopore sequencing are presented in subsequent figures.

Figure 3:
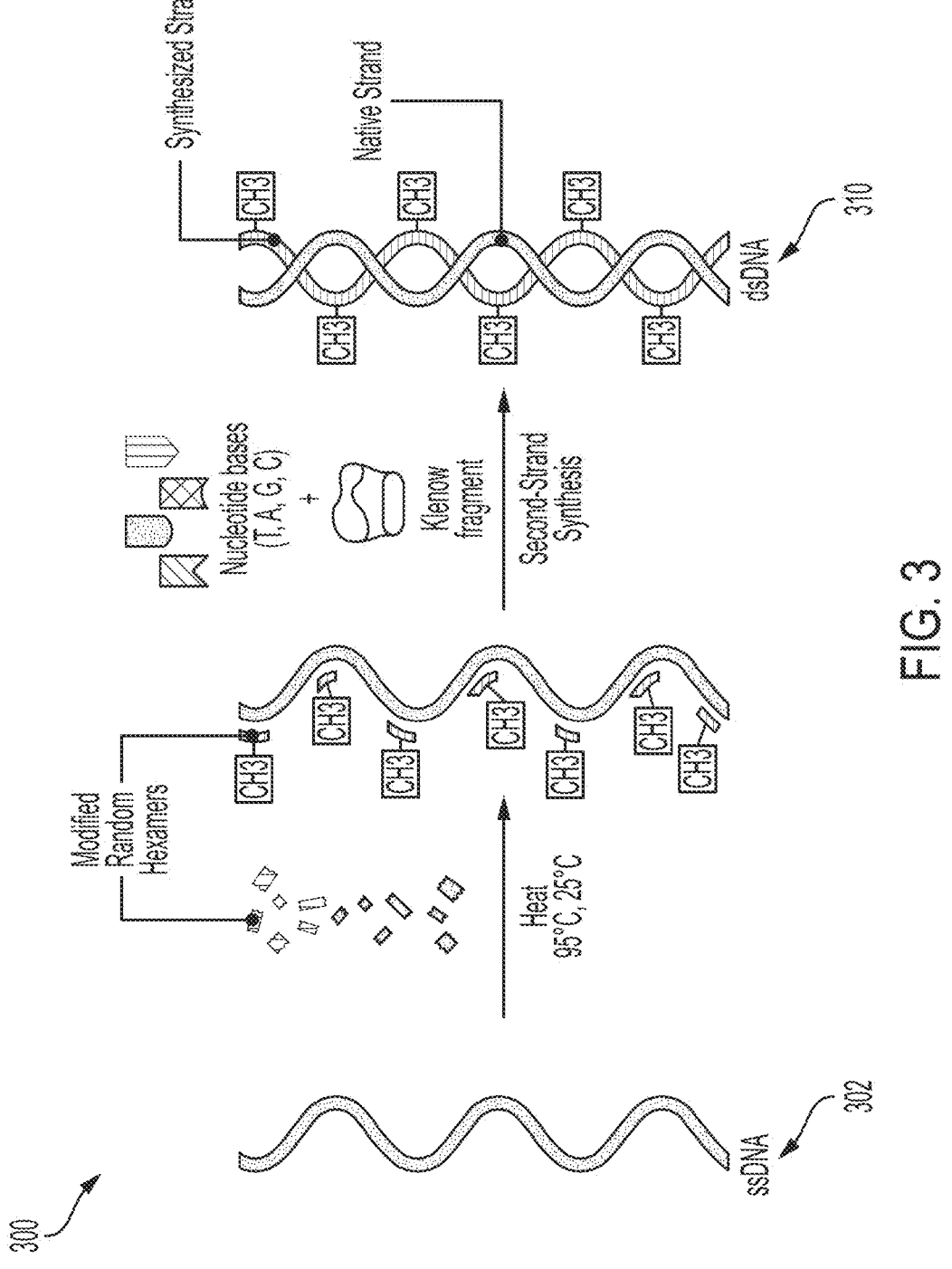
FIG. 3 illustrates a process for second strand synthesis in accordance with an embodiment of the present disclosure, showing incorporation of a modified base and selective labeling of a synthetic second strand. "CH$_3$" refers to methylated.

In various embodiments of the methods discussed herein, an example of second strand synthesis 300 is illustrated in FIG. 3. A native ssDNA strand 302 (which may be similar to ssDNA genome 204 of FIG. 2) may be used as a template to synthesize a synthetic DNA strand complementary to the native ssDNA strand 302. The second strand synthesis is catalyzed by a Klenow fragment in the presence of nucleotide bases and modified random hexamers. The second strand synthesis reaction utilizes a modified base to selectively label the synthetic DNA strand. In various embodiments of the method, the modified base comprises 5-methylcytosine, 5-hydroxymethylcytosine, or N6-methyldeoxyadenosine. In some cases, the modified base is 5-methylcytosine. The second strand synthesis leads to the formation of a double-stranded DNA product 310 with the synthetic DNA strand methylated ($CH_3$), as shown in FIG. 3.

Figure 4:
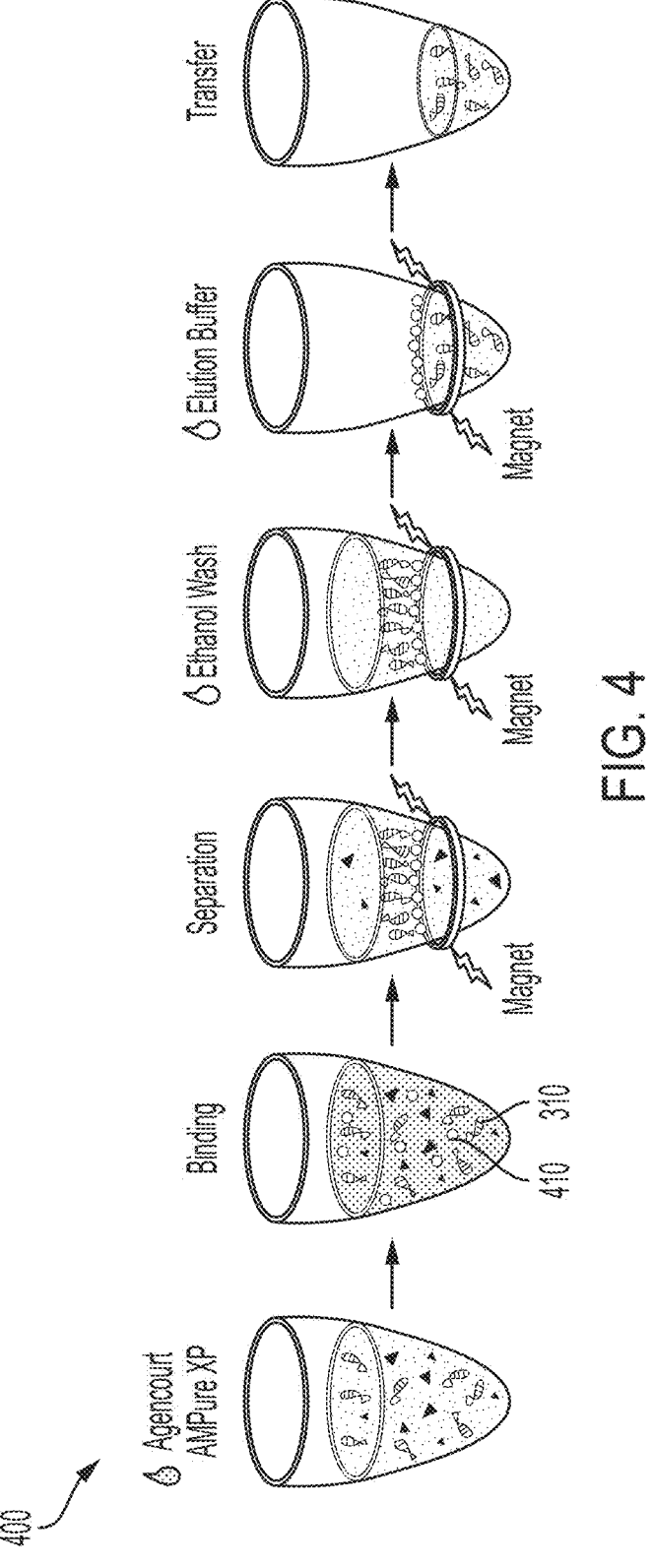
FIG. 4 illustrates the purification of the second strand synthesis product using magnetic beads.

The labeled double-stranded DNA product 310 is then purified from the second strand synthesis reaction. An example purification method 400 is illustrated in FIG. 4, which shows purification of the labeled double-stranded DNA product 310 using magnetic beads 410. The labeled dsDNA product 310 is conjugated to the magnetic beads 410 and is separated from the second strand synthesis reaction using a magnet. The labeled dsDNA product 310 is then washed and eluted from the magnetic beads 410.

Figure 5:
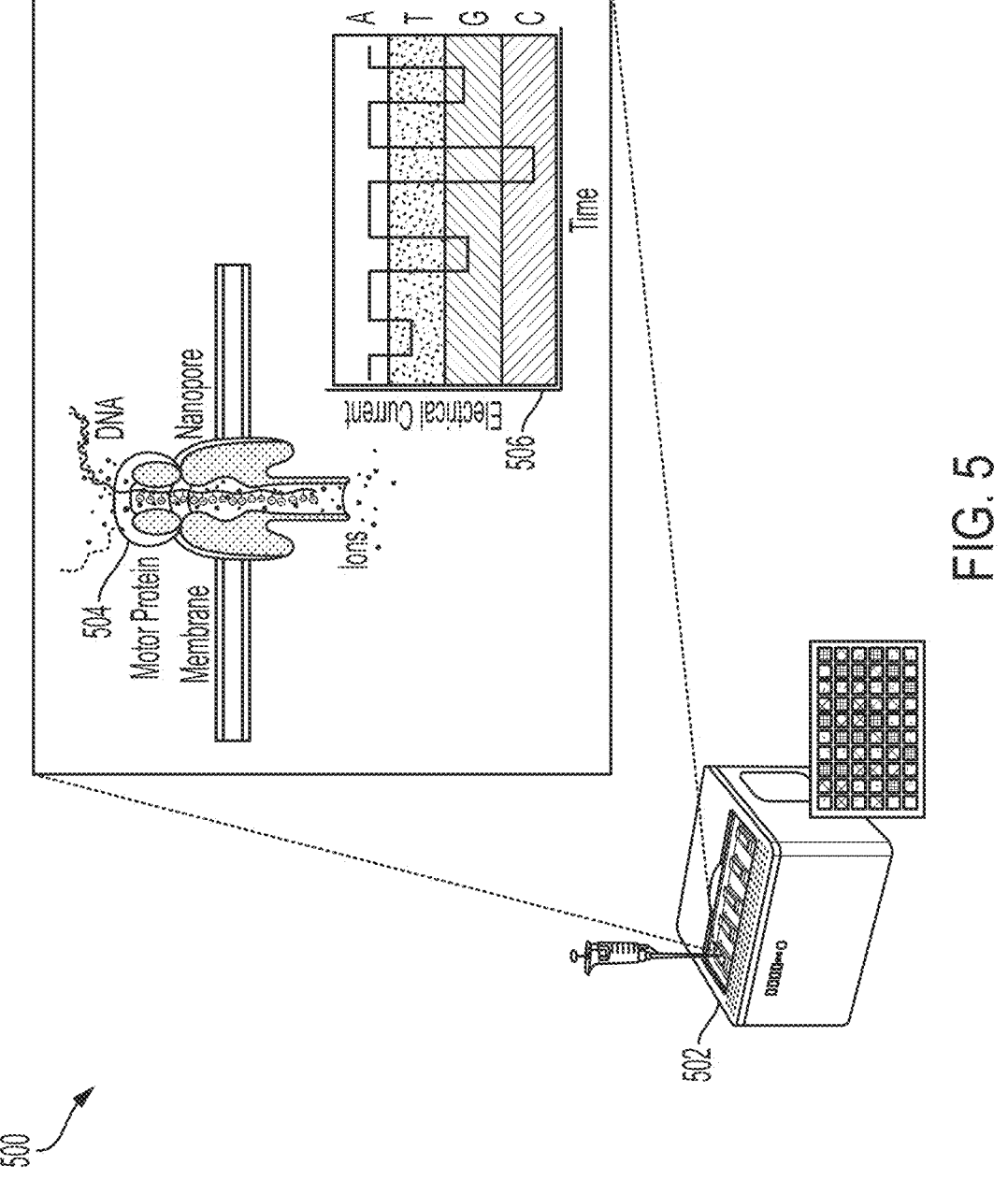
FIG. 5 illustrates sequencing of the second strand synthesis product on a nanopore sequencer and determining the sequence of a sequenced strand based on an alteration of a flow of current through the nanopore sequencer.

In embodiments of the methods discussed herein, the purified double-stranded DNA product is finally submitted for sequencing. As illustrated in FIG. 5, the sequencing 500 of the product of second strand synthesis is performed on a nanopore sequencer 502 using long-read technologies that provide single reads of from about 100 base pairs to 1000 kb or more. As shown, a nanopore 504 of the nanopore sequencer 502 identifies a sequence of nucleotides in one sequenced strand of the double-stranded DNA product. The identification of the nucleotide sequence in the sequenced strand is based on the ability of each nucleotide base to be able to alter the flow of current uniquely while passing through the nanopore 504. A plot 506 showing each base altering the flow of electrical current with time is depicted in FIG. 5. In examples, the double-stranded DNA product need not be fragmented for sequencing, thereby allowing for reads up to the length of the entire viral (e.g., AAV) genome. In various embodiments, the number of nucleotides sequenced without fragmentation is from about 100 to about 1,000,000. In some cases, the number of nucleotides sequenced without fragmentation is from about 100 to about 10,000. In some cases, the number of nucleotides sequenced without fragmentation is from about 100 to about 9000, to about 8000, to about 7000, to about 6000, or to about 5000 (e.g., the nucleotides in the sequenced strand).

The resulting sequencing data is analyzed for the presence of the modified base in the sequenced strand of the dsDNA product. The chemical structures of unmodified nucleobase cytosine and modified nucleobase 5-methylcytosine with an additional methyl group ($CH_3$) are depicted in FIGS. 6A and 6B, respectively. Both modified and unmodified nucleobases alter the flow of current differently through the nanopore. As shown in FIG. 6C, a detection of the modified base during sequencing indicates that the sequenced strand is the synthetic DNA strand of the double-stranded DNA product, as the synthetic DNA strand is modified (e.g., methylated). However, an absence of the modified base during sequencing indicates that the sequenced strand is the native DNA strand of the double-stranded DNA product, as the native DNA strand is non-methylated. A plot 610 showing an alteration of the flow of electrical current with time corresponding to the methylated (modified) and non-methylated (unmodified) strands is depicted in FIG. 6C.

The methods discussed herein include determining a specificity of the native DNA strand by identifying a specificity of the sequenced strand. The specificity of the native DNA strand of AAV genome can be determined by identifying a complementary nucleotide sequence corresponding to the complete sequence, if the sequenced strand is the synthetic DNA strand of the double stranded DNA product. Furthermore, a proportion of each of a sense strand and an anti-sense strand packaged in the sample of AAV particles can be identified based on detection of the modified base of the synthetic DNA strand.

Viral Particles

In certain aspects, the viral particle is an AAV particle and the methods disclosed can be used to determine the specificity of the ssDNA genome and identify a proportion of each of a sense strand and an anti-sense strand packaged in a sample of AAV particles. The AAV particles may be recombinant AAV (rAAV) particles. The rAAV particle includes an AAV vector encoding a heterologous transgene or heterologous nucleic acid molecule.

In certain aspects, the AAV particles include an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof. In certain aspects, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some embodiments, the AAV particles are of serotype AAV1 or AAV8.

While AAV was the model viral particle for this disclosure, it is contemplated that the disclosed methods can be applied to characterize a variety of viruses, for example, the viral families, subfamilies, and genera. The methods of the present disclosure may find use, for example, in characterizing viral particles to monitor or detect relative abundance of each of a sense strand and an anti-sense strand packaged in a composition of viral particles during production, purification or storage of such compositions.

In exemplary embodiments, the viral particle belongs to a viral family selected from the group consisting of Parvoviridae.

In certain aspects, the viral particle belongs to a viral genus selected from the group consisting of Ambidensovirus, Brevidensovirus, Hepandensovirus, Iteradensovirus, Penstyldensovirus, Amdoparvovirus, Aveparvovirus, Bocaparvovirus, Copiparvovirus, Dependoparvovirus, Erythroparvovirus, Protoparvovirus, and Tetraparvovirus.

In some aspects, the viral particle (e.g., AAV particle) contains a heterologous nucleic acid molecule or exogenous gene (e.g., a therapeutic gene or gene of interest). In some aspects, the heterologous nucleic acid molecule is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit .beta.-globin promoter and the elongation factor 1-alpha promoter (EF1-alpha) promoter. In some aspects, the promoter comprises a human .beta.-glucuronidase promoter or a cytomegalovirus enhancer linked to a chicken .beta.-actin (CBA) promoter. The promoter can be a constitutive, inducible or repressible promoter. In some aspects, the invention provides a recombinant vector comprising a nucleic acid encoding a heterologous transgene of the present disclosure operably linked to a CBA promoter. In some cases, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further aspect, other native expression control elements, such as enhancer elements, polyadenylation sites or Kozak consensus sequences may also be used to mimic the native expression.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Characterization of Viral ssDNA Genome of AAV Particles

AAV samples of different serotypes were prepared in-house. The total nucleic acid (ssDNA genome) was extracted from AAV cultured in a human host. The nucleic acid extract was subjected to second strand synthesis incorporating a modified base to yield a labeled dsDNA product. The dsDNA product was purified from the second strand synthesis reaction using an Agencourt AMPure XP Beads (Beckman Coulter). Sequencing of the purified dsDNA product was performed on a GridION nanopore sequencer (Oxford Nanopore Technologies) and the data was analyzed using bioinformatics analysis.

Chemicals and Reagents

Unless otherwise stated, all chemicals and reagents were acquired from MilliporeSigma (Burlington, MA, USA). AAV samples and their nucleic acid extract were provided in-house (Regeneron Pharmaceuticals Inc., Tarrytown, NY, USA). Agencourt AMPure XP Beads were acquired from Beckman Coulter (Indianapolis, IN, USA). Sigma-Aldrich molecular grade 200 proof ethanol was acquired from MilliporeSigma. Oxford Nanopore Technology Flow Cell Priming Kit and Oxford Nanopore Technology Rapid Sequencing Kit were purchased from Oxford Nanopore Technologies (Oxford, UK). 1.5 ml DNA/RNA LoBind Tubes were acquired from VWR (Atlanta, GA, USA). NEB Individual dNTPs and NEB Modified 5mC dCTPs were acquired from Thermo Fisher Scientific (Waltham, MA, USA). Modified random hexamers were purchased from Integrated DNA Technologies (Coralville, IA, USA).

Second Strand Synthesis Experiment

The second strand synthesis reaction was performed on total nucleic acid extract of AAV. A dNTP master mix was prepared with each of a dATP, dTTP, dGTP, and dCTP (5mC) at a working concentration of 10 mM. The reaction mixture was prepared in nuclease-free water. To the reaction mixture, 1 μg total nucleic acid extract, 10 mM dNTP master mix, and 60 μM modified random hexamer (primer) were added. The reaction mixture was heated to 95° C. for three minutes and then was allowed to cool gradually at room temperature for 10 minutes. Subsequently, 2 U/μL Klenow enzyme was added to the reaction mixture and the reaction mixture was incubated for 1 hour at 30° C. The second strand synthesis reaction was stopped by incubating the reaction mixture at 75° C. for 10 min.

Purification of Second Strand Synthesis Product

The second strand synthesis reaction was placed in a 1.5 mL DNA/RNA LoBind tube prior to the purification assay. The purification of dsDNA product from second strand synthesis reaction was performed using Agencourt AMPure XP Beads (magnetic beads). The dsDNA product was first conjugated to magnetic beads by adding resuspended AM Pure XP beads to the second strand synthesis reaction in a 1:1 ratio. The mixture of magnetic beads and second strand synthesis reaction was incubated on a mixer set at moderate agitation for 5 minutes and then briefly centrifuged. The tube containing the mixture of magnetic beads and second strand synthesis reaction was subsequently placed on a magnetic stand for 3 minutes until magnetic beads are against tube wall. The supernatant was discarded without disturbing the magnetic beads. A first ethanol wash was performed by resuspending the magnetic beads conjugated to dsDNA in 80% ethanol. The tube was then placed again on the magnetic stand for 3 minutes until magnetic beads are against tube wall and the supernatant was discarded without disturbing the magnetic beads. The magnetic beads conjugated to dsDNA was given a second ethanol wash with 80% ethanol in a similar manner. Finally, the dsDNA was eluted from the magnetic beads by resuspending the beads in a nuclease-free water with a gentle stirring motion or agitation for 5 minutes. The tube containing NFW and magnetic beads was briefly centrifuged and placed on the magnetic stand for 5 minutes until the beads form a pellet against the tube wall and the aqueous solution containing the amplicons appears clear. The aqueous solution (eluate) was then removed and transferred to a 0.2 mL PCR tube for storage and the magnetic beads are discarded.

Nanopore Sequencing of Purified Second Strand Synthesis Product

Sequencing of the purified dsDNA product was performed on a GridION nanopore sequencer (Oxford Nanopore Technologies, Oxford, UK). The GridION sequencer and flow cell were prepared for sequencing by gently placing the flow cell in designated GridION slot. The number of active pores for sequencing was verified to be 1000 or greater. The flow cell was primed using the Flow Cell Priming Kit (Oxford Nanopore Technologies, Oxford, UK) and checked for fluid flow without introducing any air bubbles. After allowing the flow cell to remain undisturbed for at least 15 minutes, the SpotON sample port cover was gently lifted to make the SpotON sample port accessible. Subsequently, the purified dsDNA product was prepared for sequencing to form a sequencing template library. Briefly, 1000 ng of the purified dsDNA product was fragmented to an average size of ~800 base pairs, end repaired, and ligated to sequencing adapters using the Rapid Sequencing Kit (Oxford Nanopore Technologies, Oxford, UK). This sequencing template library was mixed with flow cell loading mixture and the entire volume was added to the flow cell of the sequencer via the SpotON sample port in a dropwise fashion ensuring no air bubbles exist. The SpotON sample port cover was gently replaced, flow cell priming port was closed, and sequencing on the nanopore sequencer was initiated using standard protocols. The sequencing was terminated automatically at the end of 48 hours.

Data Analysis

Upon termination of sequencing, FASTQ files was transferred to AWS cloud infrastructure platform for bioinformatics analysis. The resulting sequencing data was analyzed for the presence of modified bases in a sequenced strand of the dsDNA product. The metrics for nanopore-based sequencing included absolute current flow at a given time, a duration of a given current flow measure, a duration of time the current measure indicates the detection region does not comprise a nucleobases, a duration of time between current measures that are indicative of a particular base, a magnitude of change from a base line current measure, and a magnitude of change from a prior subsequent current measure.

Results and Discussion

An example method (schematic illustrated in FIG. 2) was utilized for assaying AAV particles for strand-specificity. The method implemented second strand synthesis of isolated ssDNA genome of AAV particles (FIG. 3), magnetic bead assisted purification of second strand synthesis product (FIG. 4), and nanopore sequencing of second strand synthesis product for 48 hours (FIG. 5). Following sequencing, the specificity of the isolated single-stranded AAV genome was determined by identifying the specificity of the sequenced strand (FIGS. 6A, 6B, and 6C).

In the second strand synthesis reaction, a synthetic DNA strand was synthesized complementary to the native strand of the isolated ssDNA genome of AAV. A modified base (5mC-dCTP) was incorporated into the second strand synthesis reaction which causes the synthetic DNA strand to be methylated, resulting in a selective labeling of the synthetic DNA strand. Thus, this reaction yields a dsDNA product with the synthetic DNA strand labeled. Labeling of the synthetic second strand allows for greater resolution of positive sense versus negative sense strands. Following second strand synthesis, the labeled dsDNA product was purified from the second strand synthesis reaction using magnetic beads. The labeled dsDNA product was first conjugated to and then eluted from the magnetic beads after separating it from the rest of the second strand synthesis reaction.

Nanopore sequencing of the purified dsDNA product utilized long-read sequencing technologies that provide single reads of from about 100 base pairs to 1000 kb or more. In embodiments, the purified double-stranded DNA product need not be fragmented for sequencing, which allows for reads up to the entire length of the viral (e.g., AAV) genome. The long reads are especially useful for determining where the short-reads map, which helps with the assembly of the metagenomic sample into larger contigs and with whole genome assembly. The nanopore sequencer identifies the sequence of nucleotides in one sequenced strand of the double-stranded DNA product (as shown in FIG. 6C).

Single molecule sequencing reactions using nanopore sensors is centered around characterization of changes in current through the nanopore itself, e.g., the rate at which current fluctuations indicate a "next" base in the template is in the detection region of the pore, as well as the magnitude of the current fluctuations themselves as well as all aspects of noise that are measured during those fluctuations. The current flow is altered uniquely by each base as the template passes through the nanopore (FIG. 5). In addition, a modified nucleobase in the template is also detected by an alteration of the flow of current through the nanopore, as opposed to its unmodified counterpart (FIG. 6C). Further, where a protein (e.g., helicase or polymerase) is used to drive the template through the nanopore, interactions of the protein with the template prior to its entry into the pore can affect the kinetics of sequence detection of the portion of the template within the detection region of the pore. In this way, an upstream modified nucleobase can affect detection of an unmodified base within the nanopore.

The resulting sequencing data was analyzed for the presence of the modified base (5mC-dCTP) in a sequenced strand of the dsDNA product. The reads can be grouped based on similarity of the motifs that have the modified base. For example, the reads having methylation/modification patterns were grouped into a first group, and the reads not having methylation/modification patterns were grouped into a second group. The detection of the modified base or 5mC indicates that the sequenced strand is the synthetic DNA strand of the double-stranded DNA product, while the absence of the modified base or 5mC indicates that the sequenced strand is the native DNA strand of the double-stranded DNA product (see, e.g., FIGS. 6A, 6B, and 6C).

The specificity of the isolated single-stranded AAV genome was determined by identifying a complementary nucleotide sequence corresponding to the complete sequence, if the sequenced strand is the synthetic DNA strand of the double stranded DNA product. Furthermore, a proportion of each of a sense strand and an anti-sense strand packaged in the sample of AAV particles was identified based on detection of the modified base of the synthetic DNA strand.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for assaying a sample of viral particles comprising a single-stranded DNA genome for strand-specificity, comprising:

(a) synthesizing a synthetic DNA strand complementary to a native DNA strand of the sample of viral particles to yield a double-stranded DNA product, the synthetic DNA strand being synthesized by incorporating a modified base;

(b) purifying the synthesized double-stranded DNA product;

(c) sequencing the purified double-stranded DNA product on a sequencer, wherein the sequencer identifies the sequence of nucleotides in one sequenced strand of the double-stranded DNA product; and (d) determining the specificity of the native DNA strand by identifying the specificity of the sequenced strand, and detecting whether the sequenced strand contains the modified base, wherein the presence of the modified base indicates that the sequenced strand is the synthetic DNA strand of the double-stranded DNA product.

2. The method of claim 1, wherein the sample of viral particles comprises adeno-associated virus (AAV) particles.

3. The method of claim 2, wherein the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

4. The method of claim 1, wherein the modified base comprises 5-methylcytosine, 5-hydroxymethylcytosine, or N6-methyldeoxyadenosine.

5. The method of claim 4, wherein the modified base is 5-methylcytosine.

6. The method of claim 1, wherein the double-stranded DNA product is purified using magnetic beads.

7. The method of claim 1, wherein the sequencer is a nanopore sequencer.

8. The method of claim 7, wherein the nanopore sequencer allows entry of either the native DNA strand or the synthetic DNA strand of the purified double-stranded DNA product for sequencing.

9. The method of claim 7, wherein detection of the modified base distinguishes the synthetic DNA strand from the native DNA strand entering the nanopore sequencer.

10. The method of claim 1, wherein the native DNA strand or the synthetic DNA strand is sequenced using a long-read sequencing approach.

11. The method of claim 1, wherein the modified base of the synthetic DNA strand is detected by an alteration of a flow of current through a nanopore sequencer.

12. The method of claim 1, further comprising identifying a percentage of sense strand and anti-sense strand packaged in the sample of viral particles based on detection of the modified base of the synthetic DNA strand.

13. The method of claim 1, wherein the viral particles comprise an exogenous gene in the single-stranded DNA genome.

14. The method of claim 13, wherein the exogenous gene is a therapeutic gene.

15. The method of claim 1, further comprising determining a complete sequence of the sequenced strand.

16. The method of claim 15, further comprising identifying a complementary nucleotide sequence corresponding to the complete sequence, if the sequenced strand is the synthetic DNA strand of the double stranded DNA product.

17. The method of claim 1, wherein the sequencing identifies from about 100 to about 5000 nucleotides in the sequenced strand.

18. The method of claim 17, wherein the sequencing identifies from 100 to 1000 nucleotides in the sequenced strand.

19. The method of claim 18, wherein the sequencing identifies from 100 to 500 nucleotides in the sequenced strand.

20. The method of claim 1, wherein the sequencing is performed without fragmentation of the sequenced strand.

21. A method for distinguishing between a native DNA strand and a synthetic DNA strand in a sample of adeno-associated virus (AAV) particles comprising a single-stranded DNA genome, comprising:

(a) synthesizing the synthetic DNA strand complementary to the native DNA strand to yield a double-stranded DNA product, the synthetic DNA strand including a modified base which selectively labels the synthetic DNA strand;

(b) purifying the double-stranded DNA product;

(c) sequencing the purified double-stranded DNA product on a nanopore sequencer; and (d) determining the specificity of the native DNA strand by identifying the specificity of the sequenced strand, and detecting whether the sequenced strand contains the modified base of the synthetic DNA strand during nanopore sequencing by detecting an alteration of a flow of current through the nanopore sequencer, wherein the presence of the modified base indicates that the sequenced strand is the synthetic DNA strand of the double stranded DNA product.

22. The method of claim 21, wherein the modified base comprises 5-methylcytosine, 5-hydroxymethylcytosine, or N6-methyldeoxyadenosine.

23. The method of claim 22, wherein the modified base is 5-methylcytosine.

24. The method of claim 21, wherein the native DNA strand or the selectively labeled synthetic DNA strand is sequenced using a long-read sequencing approach.

25. The method of claim 21, wherein the double-stranded DNA product is purified using magnetic beads.

26. The method of claim 21, wherein the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

* * * * *